: (12) United States Patent
Gros

(10) Patent No.: US 9,352,074 B2
(45) Date of Patent: May 31, 2016

(54) ANTIMICROBIAL EXAMINATION GLOVES

(71) Applicant: Robert Timothy Gros, London (GB)

(72) Inventor: Robert Timothy Gros, London (GB)

(73) Assignee: CHEMICAL INTELLIGENCE LIMITED, Shropshire (GB)

( * ) Notice: Subject to any disclaimer, the term of this patent is extended or adjusted under 35 U.S.C. 154(b) by 0 days.

(21) Appl. No.: 13/986,750

(22) Filed: Jun. 3, 2013

(65) Prior Publication Data

US 2016/0058921 A1 Mar. 3, 2016

(51) Int. Cl.
| | |
|---|---|
| *C08J 7/04* | (2006.01) |
| *A01N 25/34* | (2006.01) |
| *A61K 9/14* | (2006.01) |
| *A61K 33/38* | (2006.01) |
| *A61K 38/00* | (2006.01) |
| *C07C 279/00* | (2006.01) |
| *A61L 31/16* | (2006.01) |
| *C08J 5/02* | (2006.01) |
| *A61L 31/04* | (2006.01) |
| *A61L 31/14* | (2006.01) |
| *A61B 19/04* | (2006.01) |
| *B65B 55/04* | (2006.01) |
| *B65B 55/12* | (2006.01) |

(52) U.S. Cl.
CPC ............... *A61L 31/16* (2013.01); *A61B 19/045* (2013.01); *A61L 31/049* (2013.01); *A61L 31/141* (2013.01); *A61L 31/143* (2013.01); *B65B 55/04* (2013.01); *B65B 55/12* (2013.01); *C08J 5/02* (2013.01); *A61L 2300/102* (2013.01); *A61L 2300/104* (2013.01); *A61L 2300/20* (2013.01); *A61L 2300/204* (2013.01); *A61L 2300/206* (2013.01); *A61L 2300/404* (2013.01); *A61L 2400/12* (2013.01); *C08J 2309/04* (2013.01)

(58) Field of Classification Search
None
See application file for complete search history.

*Primary Examiner* — Jeffrey T Palenik
(74) *Attorney, Agent, or Firm* — Finnegan, Henderson, Farabow, Garrett & Dunner, LLP

(57) ABSTRACT

A method of manufacturing nitrile rubber latex medical examination gloves during which (a) the glove formers are dipped into a coagulant solution containing divalent calcium cations and calcium nitrate particles, to which has been added a composition comprising Alcohol ethoxylate, Amine oxide, Ethylenediaminetetracetic acid, Glutaraldehyde, Chlorhexidine di-gluconate, Chlorhexidine di-hydrochloride, Salisept, Titanium Dioxide, nano particle silver; and during which (b) the coated glove formers are then dipped into a nitrile rubber latex dispersion to which has been added a composition comprising Alcohol ethoxylate, Amine oxide, Lactic acid, Ethylenediaminetetracetic acid, Glutaraldehyde, Salisept; and during which (c) the nitrile rubber latex gloves are finally placed in to packaging utilizing a clear coat varnish that it is impregnated with a phenolic chlorine compound, micronized nanosilver colloid, and a quaternary compound.

6 Claims, No Drawings

ANTIMICROBIAL EXAMINATION GLOVES

BACKGROUND OF THE INVENTION

Medical gloves are disposable gloves used during medical examinations and procedures that help prevent the spread of infections.

There are two distinct types of medical gloves: medical examination gloves and surgical gloves. Due to the precision required in surgical operations, the sizes of surgical gloves are more precise, have greater sensitivity, and are made to a higher standard. Therefore, for the two types of medical gloves the methods of manufacture are different.

Medical gloves are made of different polymers including natural rubber latex, nitrile rubber, and vinyl PVC. Natural rubber latices are obtained from the sap of rubber trees. Nitrile rubber is made synthetically by copolymerising acrylonitrile and butadiene.

Medical gloves come unpowdered or powdered with cornstarch to lubricate the gloves, making them easier to put on the hands. Cornstarch replaced tissue irritating Lycopodium powder and talc, but since even cornstarch can impede healing if it gets into tissues, as during surgery, unpowdered gloves are being used more often during surgery and other sensitive procedures. Special manufacturing processes are used to compensate for the lack of powder. Examination gloves are non-powdered. Gloves that have been sterilized are free of microbiological contamination including bacteria. Sterile gloves are necessary for all surgical procedures and other medical purposes where there is a greater risk and danger from infection.

Sterile gloves are packaged in pairs inside sterile pouches with their own sterile field. In comparison, non-sterile gloves are packaged in boxes of 100 or 200 pairs and are used in everyday common medical activities. Glove usage in hospitals is primarily therefore non-powdered and non-sterile.

Non-Sterile Natural Rubber Latex

Natural rubber disposable examination gloves have been the traditional choice for the healthcare industry for over one hundred years. Although concerns regarding latex allergies continue, natural rubber latex gloves are unsurpassed when it comes to durability, tactile sensitivity, comfort and fit. The advantages are high tactile sensitivity, being very durable and comfortable. The disadvantages are that they are dry, and that allergy to the proteins in the natural rubber latex irritate the skin.

Non-Sterile Nitrile Rubber Latex

Due to their resilience, nitrile rubber gloves work very well in harsh, high-stress environments. Made from nitrile rubber, these synthetic examination gloves are known for providing excellent protection against a wide range of chemicals in addition to being an effective barrier against blood-borne pathogens. They provide excellent barrier protection and chemical resistance. Most importantly, nitrile rubber latex is allergen-free and provides three times more puncture resistance than standard natural rubber latex examination gloves.

Non-Sterile PVC Latex

Due to their low cost, disposable PVC latex gloves are the most economical gloves for cost conscious facilities. Made from polyvinyl chloride (PVC), these examination gloves provide standard barrier protection. In addition to being comfortable to wear, vinyl gloves have a soft feel. For a great value allergen-free choice, PVC latex examination gloves are the favourable option. However, they are less durable, have lower elongation, and there is a bad perception of them.

Colour

Examination gloves can be found in numerous colors such as blue, purple, green, or black in addition to traditional white. In general, you will find nitrite exam gloves to be purple or blue while PVC latex examination gloves remain a white hue. It is important to note that the color of an examination glove does not determine the material composition nor performance.

Texture

Another key physical characteristic of medical gloves is texture. Textured gloves are typically preferable to prevent slippage especially when handling moist or wet objects. Textured gloves are typically found either on the fingertips or completely (all over the glove). In general, PVC latex gloves are not textured because the raw material (PVC) does not make manufacturing textured gloves easy. Textured versions of gloves can be found in Natural rubber latex or Nitrile rubber latex gloves. Today, more textured gloves are used because they are generally preferred over their smooth counterparts.

Thickness

Arguably the most important glove property is the thickness of the glove. Thickness is measured typically in millimeters, or "mils". The thickness of gloves may differ throughout the glove, but the thickest areas tend to be the fingers and palm. Thickness will typically determine the level of mechanical protection and resistance to chemicals. However, the composition of the glove also determines protection.

Sterility

Sterile examination gloves are available that come in individual packaging. In most cases, sterilized medical gloves are used whenever handling patients with open wounds in order to prevent infection. Sterile examination gloves are packaged with one or two ambidextrous gloves. Packaged sterile examination gloves are also popular because they are easily carried around in a pocket, but the gloves only remain sterile until the pack is opened, after which they can pick up infections.

SUMMARY

Around 6% of the general population have latex allergy and as many as 17% of health care workers are reported to be affected. Replacing natural rubber latex gloves with nitrile rubber latex gloves will help make the clinical environment safer for staff and patients with latex allergies without sacrificing the quality of the gloves. Taking this into consideration the trend in recent years is a movement to purchase latex-free gloves. As stated above this does not necessarily mean purchasing nitrile rubber latex gloves as the lower quality yet cheaper PVC latex glove is a viable alternative.

Surgical Gloves

Surgical gloves provide comfort and tactile sensitivity whilst providing barrier protection to surgeons, nurses and patients during operating procedures. Medical surgical gloves are made from a range of materials that include natural rubber latex and polyisoprene, which vary in fit, feel, and protection. When considering which surgical glove to use, the protection level and exact fit will be one of the most important attributes to look at as well as which surgical procedure the gloves will be used for. For microsurgery and orthopedic surgeries speciality surgical gloves are available. Although natural rubber latex examination gloves have become increasingly replaced by synthetic gloves, this is not the case with surgical gloves as surgical procedures using gloves made from alternative materials generally do not fully match the fine control or greater sensitivity to touch available with natural rubber latex surgical gloves.

Other high-grade synthetic alternatives such as nitrile rubber latex gloves can cost over twice the price of their natural rubber latex counterparts, a fact that has often prevented switching to these alternative materials. In comparison to examination gloves, surgical gloves have more precise sizing with a better precision and sensitivity and are made to a higher standard.

Surgical Gloves (Natural Rubber Latex)

Natural rubber latex surgical gloves are made from natural rubber latex, which provides excellent tactile sensitivity and comfort. Natural rubber latex material is known to have very high elasticity, meaning the gloves can stretch well to allow easy donning Although surgical gloves are now available in new materials such as polyisoprene, natural rubber latex continues to be the material of choice for surgical gloves by surgeons. Today, there are many natural rubber latex glove options available due to improved technology. For instance, surgical gloves with polymer inner coating are available to provide ease of donning gloves even if hands are damp or dry. Other improvements include under glove indicators that are used while double-gloving to warn surgeons of glove punctures that may occur.

Surgical Gloves (Polyisoprene)

Polyisoprene surgical gloves are made from synthetic polyisoprene which provides similar properties to natural rubber latex. In fact, polyisoprene has a molecular structure that is very similar to natural rubber. Polyisoprene is regarded as a "latex" glove without the harmful protein found in natural rubber latex, which is responsible for latex allergies. Like other surgical glove materials, polyisoprene surgical gloves are available with polymer inner coating. So donning gloves are easier even when hands are damp or dry. Polyisoprene is the most expensive material used to make surgical gloves. Even so, most surgical glove manufacturers offer polyisoprene gloves options as adoption continues to increase due to having similar properties to natural rubber latex.

The three primary surgical glove manufacturers are Molnlycke Health Care (formerly Regent Medical), Cardinal Health, and Ansell Professional Healthcare. These manufacturers provide a wide range of natural rubber latex options which include speciality surgical gloves as well as general-use surgical gloves.

BRIEF SUMMARY OF THE INVENTION

This invention concerns a process used to manufacture and package antimicrobial medical examination gloves that are more effective than existing medical examination gloves at preventing infection and that will themselves kill infectious microorganisms on the glove, on the hand of the wearer, and on any medical equipment or on parts of the patient, touched by the medical expert's gloved hands, even if the glove suffers small tears and if the physical barrier is breached.

DETAILED DESCRIPTION OF THE INVENTION

Examination gloves are used by medical staff to prevent the transfer of infections between medical workers and their patients. They are worn by medical workers at the start of the examination and discarded and destroyed at the end of the procedure. They function by creating a physical barrier between the medical practitioner and patient that prevents the transfer of infectious microorganisms between the two parties. The gloves themselves are not sterile and there is always a danger that the gloves could tear, allowing microorganisms to be transferred between the patient and the practitioner.

We have developed a process by which the examination gloves are rendered antimicrobial and will themselves kill infectious microorganisms on the glove, on the hand of the wearer, and on any medical equipment or on parts of the patient, touched by the medical expert's gloved hands. More importantly, even if the glove suffers small tears and if the physical barrier is breached, the antimicrobial properties of the glove will ensure that infection cannot be transferred. The method of manufacture is more suitable for examination gloves rather than the manufacture of surgical gloves. We have used nitrile rubber as the primary choice of material after an assessment of the advantages and disadvantages of the possible materials that we have summarised previously.

Manufacturing Sequence

The formers on which the gloves form are mounted on a continuous conveyor belt that takes the formers through a series of dip tanks and ovens. The dip tanks, into which the formers are submerged, are continually fed with fresh solution to replace solution that is removed when the coated formers leave the tank. In addition the solution in each tank is continuously circulated to ensure that its composition remains uniform. The biocides are in a solution concentrate, which will be metered into the tank along with the regular make up solution. The composition of the solution concentrate added to the coagulation tank is different from the concentrate we add to the nitrile rubber dipping tank.

First Stage

Clean porous porcelain glove formers, mounted on a continuous conveyor belt, are dipped into the tank containing a coagulant solution containing multivalent such as calcium ions and possibly a particulate solid such as calcium nitrate.

We have found further that a number of antibacterial agents are compatible with and can be added to the coagulant solution, without affecting the manufacture of the gloves. Furthermore, the addition of these substances destroyed microorganisms that were brought in contact with the material of the glove. The following antibacterial agents were added to the calcium coagulant suspension. All, or a combination of, the following were assessed: poly(hexamethylene biguanide), benzalkonium chloride, chlorhexidine, photo-catalytic titanium dioxide, silver salts and nanoparticles, and Glutaraldyde. Substances similar to those on this list could also be considered.

The selected chemicals were identified for their antimicrobial activity and their dynamic interaction between the calcium nitrate coagulant layer and the nitrile rubber substrate. Our method of uniformed distribution of antibacterial agents using a cationic or nonionic solution, micro-emulsion or micro-dispersion enables the antimicrobial agents to be added to the coagulant solution and to physically and chemically bond the active ingredients uniformly to the surface of the nitrile rubber latex gloves.

The interaction between the coagulant and nitrile rubber latex is critical. It is not feasible to suspend all of the materials in both layers as this results in the separation of ingredients resulting in precipitation and may also contribute to the deactivation of the antimicrobial components. Precipitation significantly retards the coating process. Uniform distribution of the coagulant on to the former is critical in the quality of the end product. The antimicrobial ingredients may only be used if the correct polarity is displayed within the solution. Cations potentially cause pre coagulation of the nitrile rubber dip solution or they might interfere with the coating process as described above. The quantities of each constituent could range from 0.01% up to 1% of each active ingredient.

The selection of antimicrobial blend ensures the continued smooth operation of the manufacturing process. The active ingredients integrated into the coagulant have to emulate the same properties at the coagulant solution to achieve the same drying characteristics as the base formulation any deviation in drying time, temperature or hardness will result in an uneven or reduced coagulation propensity of the latex solutions this includes nitrile. In addition the active ingredients must also be harmonious to the coagulant solution, the calculation for the ratio of coagulant to latex has the same adverse effect if the active ingredients prevent the coagulant from coming into contact with the ingredients in the nitrile rubber latex and the uniform incorporation of the antimicrobial agents on to the particulate filler and surface of the glove. The selection of antimicrobial agents is critical during the fixing process of the coagulated nitrile rubber. Incorrect selection or distribution of the actives will result in a compromise in the integrity and efficacy of the product.

Second Stage

The formers are withdrawn from the solution and drained before passing through an oven in which the coagulant solution adhering to the formers dries.

Third Stage

The former, with dried coagulant on its surface is dipped into the tank containing an aqueous nitrile rubber latex suspension blended with other additives as required. A novel mixture of organic acid and the compound Monomeric polyglutaraldehyde, formulation was added to the nitrile rubber latex suspension. Cationic antibacterials are incompatible with the anionic ingredients in the nitrile rubber latex blend. Silver salts and nanoparticles react adversely with the sulphur present in the latex suspension. Anionic nitrile rubber latex particles are introduced to the cations suspended in the coagulant coated surface of the former in the vicinity of the cationic surface of the former. The coagulate and latex undergo a process of ion transfer and polymerisation occurs and the latex particles are deposited on the former in a thin layer. Once the thin layer has formed, the surface is sealed and no more nitrile rubber latex particles can coagulate onto the surface, limiting the thickness of the polymer coating.

Fourth Stage

The nitrile rubber latex coated former is lifted out of the nitrile rubber solution, allowed to drain, and then passes through another oven. Heating the coagulated nitrile rubber latex particles on the former evaporates the water and causes the polymer particles to coalesce and form a continuous polymer film that is the glove.

The nitrile rubber latex coated former is lifted out of the nitrile rubber solution, and allowed to drain. The un-coalesed latex and coagulant are now a mobile uniformed structure that required the final process of the formation of a uniform permanent structure. The antibacterial additives are now encapsulated within the structure of the coagulant and the latex providing protection on the internal and external surfaces due to the micro-particulate structure of the latex polymers. The former now passes through another oven. Heating the coagulated nitrile rubber latex particles on the former evaporates the water and causes the polymer particles to coalesce and form a continuous polymer film that is the glove.

Fifth Stage

The formed glove then undergoes further treatment processes, including beading. The glove is then removed from the former with a sharp blast of compressed air. This process turns the gloves "inside out", the surface of the glove on the porcelain former, in contact with the calcium coagulant suspension, becomes the outer surface of the glove. After tumble drying, the glove is inspected and packed ready for dispatch.

Sixth Stage

The former is cleaned and returned to the coagulation tank to repeat the cycle.

Seventh Stage

The medical examination gloves are inserted in to antimicrobial packaging. The principle behind the coating is to provide a microbial barrier between the environment and the packaging, thereby further protecting the antimicrobial glove from contamination. The active agents are symbiotic to the gloves. Utilising a clear coat varnish it is impregnated with a phenolic chlorine compound, micronised nano silver colloid, and a quaternary compound. The surface remains biostatic in the presence of microbial contamination maintaining a unique package to allow the antibacterial examination gloves to be uncompromised regardless of their location and their clinical environment.

The manufacturing process is novel because the antimicrobial ingredients are contained both inside and on the surface of the glove for optimum effect. In addition the antimicrobial agents are incorporated into the existing glove making process and do not require the introduction of any additional expensive processing stages.

Incorporation of Biocidal Agents

We have developed a process that incorporates a synergistic mixture of biocidal agents into the glove by adding a specially formulated mixture of biocides into the calcium coagulant suspension and/or the nitrile rubber compound suspension. The composition of both suspensions needs to be very carefully controlled to ensure that they perform as required. The coagulant suspension must remain stable, to deposit coagulant ions and calcium carbonate particles onto the surface of the clean former. The nitrile rubber suspension must deposit the layer of coagulated nitrile rubber latex particles onto the glove former. Certain ingredients might cause either suspension to coagulate without coming into contact with the former. This would cause the liquid contents of the tanks to gel, precipitate and sediment or solidify. Other ingredients might prevent the nitrile rubber latex particles from coagulating on the former, preventing the formation of the gloves.

The two suspensions are incompatible and cannot be mixed without coagulating. An important part of our invention is that we have developed methods of adding the required ingredients to the two suspensions without disrupting their performance. The approaches required for the two suspensions are quite different and so must be chosen very carefully. It is important that whatever is added to either suspension tank does not interfere with the examination glove making process.

Individual biocidal agents destroy particular infectious microorganisms. To ensure the treated gloves destroys the broad range of infections they are likely to experience, the gloves need to contain a careful selection of biocidal agents. Many substances are known to kill infectious microorganisms, while being suitable for use on the skin. However, a number of additives are not suitable for use. Some antimicrobial agents are known to sensitise the skin. Some biocides might be deactivated in the coagulant solutions or might evaporate or degrade at the temperature at which the gloves are heated in the drying oven. Some other additives are only compatible with either the coagulant suspension or the nitrile rubber suspension.

Thus certain cationic biocides, such as poly(hexamethylene biguanide) (PHMB) and chlorhexidene are known to be deactivated by the anionic surfactants used to stabilise the nitrile rubber latex and could only be used in the coagulant tank.

Other biocidal agents could be formulated into either suspension. Each biocide kills the bacteria in different ways and so mixtures will have synergistic effects. A number of biocides are insoluble in water and or are too reactive to be simply added in to a solution and need to be dispersed into a carrier prior to being added to either of the two suspensions without adversely affecting their stability and the formation of the gloves.

Finally the gloves need to protect the person wearing the gloves and/or the patient. Incorporating the biocide onto the outside surface of the glove will prevent the glove picking up an infection and infecting the patient. Biocide incorporated into the nitrile rubber layer will also protect the wearer against the danger of the glove tearing.

We have identified particular antibacterial agents and ways of incorporating them into the glove that will protect both their wearer and their patient from the dangers of cross infections. A wide range of antibacterial agents have been evaluated and a number have been found to be ineffective. Other antibacterial agents have been found to be effective. These include nano-silver dispersions, triclosan, poly (hexamethylene biguanide) (PHMB), benzalkonium chloride, chlorohexidene and photo-catalytic grades of titanium dioxide.

These agents are incorporated in the ratio and the location that is most effective at destroying microorganisms. Because of the compatibility issues described above, the use of some of the agents would be restricted to use in certain parts of the glove manufacturing process.

Some antibacterial substances are soluble or are available as stable dispersions and can be readily added to the aqueous phase. Others are difficult to disperse into water and therefore need dispersing using particular combinations of surfactant stabilising agents and technology.

Manufacture of Biocidal Concentrates

These antibacterial agents were added to the calcium coagulant suspension:

Poly(hexamethylene biguanide) (PHMB)
Chlorohexidene
Benzalkonium chloride, such as BTC 50E
Triclosan
Photo-catalytic titanium dioxide, such as Kronoclean 7000
Silver solutions and nanoparticles The following antibacterials were added to the nitrile rubber latex suspension:

Triclosan
Photo-catalytic titanium dioxide
BIT. 1,2-Benzisothiazol-3((2H)-one, such as Proxil
Phenoxyethanol
Methylchloroisothiazolinone Tests were carried out in order to assess which combination of biocidal agents were compatible with the glove manufacturing process and gave the best antimicrobial performance. Small rectangles of nitrile rubber latex were prepared by dipping clean microscope slides into warm coagulant solution, withdrawing them and drying them in an oven at 110° C. The slides were allowed to cool before dipping into the nitrile rubber latex dispersion. They were withdrawn, allowed to drain, and placed in an oven at 110° C. After cooling the layer of cured nitrile rubber was carefully removed from the microscope slide and sent for testing to determine their antimicrobial properties. Active ingredients were incorporated into the coagulant and nitrile polymer latex dispersion as appropriate.

The qualitative measure of their antibacterial performance was carried out by zones of inhibition analysis. The procedure used was for each sample to be assayed against *Staphylococcus aureus*, a bacterium commonly found on the skin of humans, by comparing their zones of inhibition on an agar preparation.

Seeded agar plates were prepared by adding 0.1 ml of an overnight broth culture into a clean, sterile petri dish, adding approximately 20 ml of an agar preparation that had been sterilised and cooled to 45° C. before use. The selective agar used was Tryptone Soy Agar. The challenge organism was mixed into the agar by gentle swirling to provide a homogeneous suspension. The plates were allowed to set for approximately one hour in a cool dry place.

Swatches of the polymer glove material were cut to approximately 2 cm square and placed on the seeded agar. The petri dishes were then placed in an incubator overnight at 37° C. Migration of the chemicals toxic to the challenge organisms creates a zone around the edge of the swatch where growth of the challenge organism is inhibited. The relative distance of the zone inhibition from the edge of the swatch for each organism gives an indication of the antibacterial efficacy of the products. The results of these experiments were as follows:

Experiment 1

This experiment showed that incorporating triclosan or BIT into the nitrile rubber latex dip bath did not affect the formation of the nitrile rubber film. Polymer films containing the two biocides exhibited antibacterial properties as they kill bacteria in the zone surrounding the glove material. The control film which did not contain the antibacterial showed no signs of bacterial inhibition.

| NITRILE RUBBER RECTANGLE | ZONE OF INHIBITION | LAB REFERENCE |
| --- | --- | --- |
| Untreated, contained no antibacterial agent | 0 mm | 12A/133 |
| Triclosan, 0.05% added to nitrile rubber | 15 mm | 12A/130 |
| Proxel (BIT) 0.15% added to nitrile rubber | 9 mm | 12A/131 |

Experiment 2

The experiment was repeated. In this trial the control sample (12B/088) showed some signs of inhibition. Triclosan was shown to be significantly more effective at concentrations as low as 0.1%, as was 0.1% BIT. Phenoxyethanol was less effective as was the silver nano-dispersion, SteriTouch ST1104.

On standing the nitrile latex dispersions containing SteriTouch showed signs of precipitation and the formation of a black material. Silver salts react with the sulphur in the nitrile rubber latex dispersion. A blend of triclosan, BIT and silver nano-particles were incorporated into one sample of glove polymer in the hope that an improved synergistic effect would be obtained.

The nitrile rubber sheet had some antibacterial performance but was not as effective as the individual ingredients. It was possible the antibacterial performance might have been adversely affected by the presence of the silver nano-dispersion.

| NITRILE RUBBER RECTANGLE | ZONE OF INHIBITION | LAB REFERENCE |
| --- | --- | --- |
| Untreated, contained no antibacterial agent | 10 mm | 12B/088 |
| Triclosan, 0.1% added to nitrile rubber | 20 mm | 12B/074 |

-continued

| NITRILE RUBBER RECTANGLE | ZONE OF INHIBITION | LAB REFERENCE |
|---|---|---|
| Triclosan, 0.25% added to nitrile rubber | 18 mm | 12B/078 |
| Proxel (BIT), 0.1% added to nitrile rubber | 15 mm | 12B/075 |
| Phenoxyethanol, 1.0% added to nitrile rubber | 8 mm | 12B/084 |
| SteriTouch ST1104, 0.5% added to nitrile rubber | 10 mm | 12B/083 |
| Triclosan 0.15%, BIT 0.15% and SteriTouch 0.15%, added to the nitrile rubber | 15 mm | 12B/087 |

Experiment 3

In the third set of experiments triclosan was shown to be effective at a concentration of 0.05% (run 12C/064) in the nitrile rubber film. 0.5% Methylchloroisothiazolinone was also shown to be an effective antibacterial agent in this application. In this set of experiments a number of cationic biocides, which would precipitate in the presence of the anionic ingredients in the nitrile rubber dispersion, were added to the calcium containing coagulant solution. The coagulant solution was dried onto the former (a microscope slide) by heating the former in an oven at 120° C. The former was dipped into the nitrile rubber solution to form the polymer film. The antibacterial agent was therefore only on one side of the nitrile rubber film, corresponding to the outside surface of the glove. This was the side of the film placed on the agar plate. The cationic biocides evaluated were chlorhexidine and benzalkonium chloride. Both gave the nitrile rubber film effective antibacterial performance. Triclosan was also incorporated into the coagulant solution (12C/074 and 075). It also exhibited antibacterial performance but was not as effective as when it was incorporated into the nitrile rubber layer. Finally, a sample that contained 0.1% triclosan in the nitrile rubber film and chlorhexidine in the coagulation layer was evaluated (12C/077). The film showed antibacterial performance but was not as good as individual components. The concentration of chlorhexidine was very high. Perhaps there was interference between the two agents.

| NITRILE RUBBER RECTANGLE | ZONE OF INHIBITION | LAB REFERENCE |
|---|---|---|
| Untreated, contained no antibacterial agent | 0 mm | 12C/078 |
| Triclosan, 0.05% added to nitrile rubber | 12 mm | 12C/064 |
| Triclosan 0.1% added to nitrile rubber | 17 mm | 12C/065 |
| Methylchloroisothiazolinone 0.5% added to nitrile rubber | 15 mm | 12C/067 |
| BTC 50E 0.22% added to coagulant solution | 14 mm | 12C/068 |
| BTC 50E 1.0% added to coagulant solution | 30 mm | 12C/070 |
| Chlorhexidine 0.1% added to coagulant solution | 11 mm | 12C/071 |
| Chlorhexidine 1.0% added to coagulant solution | 18 mm | 12C/073 |
| Triclosan 0.1% added to coagulant solution | 10 mm | 12C/074 |
| Triclosan, 0.5% added to coagulant solution | 12 mm | 12C/075 |
| Triclosan 0.1% in nitrile rubber 1.0% chlorhexidine in coagulant solution | 13 mm | 12C/077 |

Experiment 4

In the final series of experiments, triclosan was incorporated into the nitrile rubber and gave good antibacterial performance. The cationic biocides BTC 50E and PHMB were incorporated into the coagulation layer, with good results. The PHMB results showed that when the biocide is incorporated into the coagulation layer, only one side of the polymer film exhibits antibacterial performance. When triclosan is incorporated into the nitrile rubber, both sides of the film exhibit antibacterial activity. Kronoclean 7000 is a modified grade of the white $TiO_2$ pigment. It absorbs energy from UV and visible light, which degrades organic molecules. If microorganisms are present it will destroy them. Unfortunately it will also degrade nitrile rubber polymer. So it was dispersed in water and added to the coagulant solution on the surface of the glove so that it would not degrade the nitrile rubber, and so that it would absorb the most light. Kronoclean 7000 exhibited some antibacterial activity. Finally, two samples were prepared in which 0.1% triclosan was in the nitrile rubber and a cationic biocide was in the coagulant layer and both of these samples exhibited good antimicrobial performance.

| NITRILE RUBBER RECTANGLE | ZONE OF INHIBITION | LAB REFERENCE |
|---|---|---|
| Untreated, contained no antibacterial agent | 5 mm | none |
| Triclosan, 0.1% added to nitrile rubber | 16 mm | none |
| BTC 50E, 0.25% added to coagulant solution | 8 mm | none |
| PHMB*, 0.3% added to coagulant solution | 5 mm | none |
| PHMB, 0.3% added to coagulant solution | 16 mm | none |
| Kronoclean 7000, 0.5% added to coagulant solution | 10 mm | none |
| Triclosan 0.1% in nitrile rubber BTC 50E 0.2% in coagulant solution | 12 mm | none |
| Triclosan 0.1% in nitrile rubber PHMB 0.3% in coagulant solution | 21 mm | none |

*The nitrile rubber film was placed face up on the agar plate, not face down as normal. Thus the biocide was not on the side of the film on the agar gel.

Biocidal Agents

As a result of these experiments, two antibacterial concentrates have been developed, one to be added by the glove manufacturer to the coagulant tank and the other to the nitrile rubber tank. The concentration of actives in the two solutions is designed to provide the required concentration of active in the final gloves without affecting the manufacture of the gloves.

The following agents could be added to the calcium coagulant suspension:

Poly(hexamethylene biguanide) (PHMB)
Chlorohexidene
Triclosan (it is more effective when added to the nitrile rubber layer)
Photo-catalytic titanium dioxide
Benzalkonium chloride
Silver salts and nanoparticles The following agents were to be added to the nitrile rubber suspension:

Triclosan

BIT and methylchloroisothiazolinone could be added to the nitrile rubber suspension but their use has been rejected because of they irritate the skin. The concentrate for the cationic tank is an aqueous solution stabilised by cationic or the minimum quantity of nonionic surfactants. The concentrate design to be added to the nitrile rubber latex tank is an aqueous dispersion stabilised by anionic or the minimum quantity of nonionic surfactants.

Our experiments have also shown it is possible to add the antibacterial agents into the nitrile rubber and the coagulant layers.

A number of the anti-microbial agents used are soluble in water, whilst others are available in water dispersible solutions or dispersions. One, triclosan, is a powder that is difficult to disperse in water. Triclosan is only very slightly soluble in water (0.0012 g per liter), and for practical purposes it does not dissolve in water.

The nitrile rubber glove dipping solution/dispersion is water based. Triclosan has previously been used by adding triclosan to natural rubber latex by mixing triclosan powder into water as a paste or by ball milling triclosan for five hours to form a dispersion.

Triclosan powder has a large particle size, of about 100-1000 micron. Mixing triclosan into water as a paste will not reduce this particle size. The particles will be very large, and significant relative to the thickness of the glove, and therefore are likely to weaken the mechanical properties of the glove. Because the particles are large they will tend to settle out unless the solution is vigorously agitated. Worse still, because triclosan is present as large particles the number of particles present will be relatively small. Its distribution throughout the glove will be very poor. Some areas next to particles will contain large amounts of triclosan, whilst others where there are no particles will be triclosan free. Due to triclosan's very low water solubility, and the inadequacies of previous methods used we have developed a special and novel technology, which does not involve the use of solvents in order to prepare a water stable diluteable dispersion.

The triclosan powder is added to the required quantity of water containing the required quantity of the appropriate surfactants. The mixture is heated up to 60-70° C. The melting point of triclosan is 55-57° C. The mixture is stirred vigorously to disperse the liquid triclosan into small (<<20 µm diameter) non-settling droplets which are stabilised by the surfactant. When the dispersion has been completed, the dispersion can be cooled to room temperature which solidifies the triclosan droplets. This gives a dispersion of micron sized triclosan particles in water. Because of our careful choice of surfactants this dispersion is stable (the particles do not increase in size for many weeks). Only certain combinations and amounts of surfactants produce stable dispersions.

The dispersion concentrate can then be added to the nitrile rubber latex. The triclosan stabilising surfactants are compatible with those in the nitrile rubber latex. The tiny particles are uniformly dispersed throughout the latex. Because the particles are so small their number is very high so the distribution of triclosan throughout the dispersion and eventually throughout the nitrile rubber of the glove is very uniform. Thus the concentration of triclosan required to give good antimicrobial performance is only 0.05 to 0.25% triclosan.

Where triclosan was not the active ingredient of choice it is possible to substitute the triclosan compound with an alternative organic compound. In this case glutaraldehyde was selected. This required the method of addition to be via a premixed solution of amphoteric surfactants and non-ionic surfactants to prevent the latex being shocked or 'intank' coagulation taking place. The method and distribution of active ingredients was verified by testing the coagulant solution and the latex solution prior to preparing the finished glove. Further testing was then carried out on production gloves using this method of manufacture.

An alternative method of dispersing triclosan into water is by dissolving it in a water miscible solvent such as an alcohol or acetone and then adding the solution to water. On hitting the water the triclosan precipitates out as small particles. The solvent mixes with water. These small particles slowly, over a period of hours, coalesce and increase in size. Unfortunately, the nitrile rubber latex glove contains solvent (VOC) which is given off as a vapour when the coated formers are dried in the hot ovens.

We have found that of the anionic surfactants, sodium dodecyl benzene sulphonate is effective at dispersing triclosan in water but surprisingly, closely related sodium lauryl sulphate, is not. We have also found that non-ionic surfactants such as alkyl alcohol ethoxylate nonionics are also effective. Mixtures of sodium dodecyl benzene sulphonate and alky alcohol ethoxylate can also be used to disperse triclosan.

If the emulsion has been stabilised by the nonionic surfactant it can be added to the coagulant or nitrile rubber latex solution. If it has been stabilised by the anionic surfactant it can only be used in the nitrile rubber latex bath. Thus three types of antibacterial blend concentrates can be prepared, one suitable for the cationic coagulant tank, the second for the anionic latex tank and nonionic stabilised concentrates that can be added to either tank.

In this way biocidal additives can be added to the coagulant tank. They are present in the layer of liquid which wets the surface of the former when it is removed from the coagulation tank and is fixed on the formers surface when it is dried in the oven. Thus the actives are deposited on the outside surface of the final glove. Biocidal actives can be added and dispersed in the tank containing the nitrile rubber latex particles. When the latex particles coagulate onto the surface of the former, they trap the aqueous latex continuous phase between the latex particles. The entrapped solution is carried into the oven dryer where the water evaporates, leaving the appropriate quantity of antibacterial agent uniformly distributed and fixed in the bulk of the glove.

The presence of the antibacterial agent mixture on the surface and in the bulk of the glove ensures that no microorganisms can grow on the glove. Thus they will remain sterile. In addition, the agents are sufficiently persistent and stable to retain their activity when the gloves are worn. Thus they are able to destroy any infection on the hands of the wearer and any surface that the gloves touch and to provide protection against infection if the gloves suffer minor tears.

It will be clear to the reader that, as well as this process enabling the production of antimicrobial nitrile rubber latex gloves, it could also be used to produce antimicrobial natural rubber gloves.

By modifying the formulation of the antimicrobial concentrate (that is, making it compatible with the plasticiser in the PVC plastisol), it can also be used to manufacture antiseptic PVC latex gloves. It is possible to make use of the methods described to produce gloves for surgical purposes, or other unspecified purposes, in which the prevention of infection is either essential of preferred.

Final Formulation Review

We carried out additional research to identify functional activity in the pre coagulated solutions. We conducted a number of studies based on a specific formulations with targeted ingredients this research has identified the most synergistic ratios for both the coagulant formulation and the latex formulation. Whilst these ratios may be required to be modified for specific applications the most synergistic blend of ingredients have been shown to be. The coagulant formulation is produced by the addition of a pre-solubilised combination of biocides in a Zwitterionic suspension to the calcium nitrate coagulant. The total addition rate of the suspension is between 0.9% and 5%. The suspension is mixed until this is clear and the ingredients are evenly distributed within the structure. This is a critical aspect of the development as the substructure prevents polarisation of the cationic active ingredients These include but are not exclusively between:

1% to 3% of an non-ionic surfactant—Alcohol ethoxylate 0.1% to 0.5% of an amphoteric surfactant—Amine oxide 0.1% to 0.5% of a chelate—Ethylenediaminetetraacetic acid 0.1% to 0.5% of an organic biocide—Glutaraldehyde 0.5% to 1% of a cationic biocide—Chlorhexidine di gluconate 0.5% and 1% of a cationic biocide—Chlorhexidine di hydrochloride 0.1% to 0.25% of a cosmetic biostatic—Salisept (4-Isothiazolin-3-one, 5-chloro-2 methyl-; 3(2H)-Isothiazolone)

Titanium Dioxide and nano particle silver is dispersed directly into the calcium nitrate coagulant solution at a concentration not exceeding 0.2%.

The Latex suspension was also assessed and the following formulation was identified as exceeding previous development samples:

0.1% to 0.3% of an non-ionic surfactant—Alcohol ethoxylate 0.1% to 0.25% of an amphoteric surfactant—Amine oxide 0.1% to 0.3% of an organic acid—Lactic acid 0.1% to 0.5% of a chelate—Ethylenediaminetetracetic acid (Na 4 EDTA)

0.1% to 0.5% of an organic biocide—Glutaraldehyde 0.1% to 0.25% of a cosmetic biostatic—Salisept (4-Isothiazolin-3-one, 5-chloro-2 methyl-; 3(2H)-Isothiazolone)

The ingredients are pre-mixed in to a stable uniform solution and then added to the latex tank at a rate of between 0.3% and 0.9%. Higher concentrations may be used but we have intended to identify the minimum inhibitory concentration rate for commercial reasons. The latex content is balanced and held at concentration of 30% latex solids.

Example

A preferred example is a method of manufacturing nitrile rubber latex medical examination gloves during which (a) the glove formers are dipped into a coagulant solution containing divalent calcium cations and calcium nitrate particles, to which has been added a composition comprising 1% to 3% Alcohol ethoxylate, 0.1% to 0.5% Amine oxide, 0.1% to 0.5% Ethylenediaminetetracetic acid, 0.1% to 0.5% Glutaraldehyde, 0.5% to 1% Chlorhexidine di-gluconate, 0.5% and 1% Chlorhexidine di-hydrochloride, 0.1% to 0.25% Salisept, less than 0.2% Titanium Dioxide, less than 0.2% nano particle silver; and during which (b) the coated glove formers are then dipped into a nitrile rubber latex dispersion to which has been added a composition comprising 1% to 3% Alcohol ethoxylate, 0.1% to 0.5% Amine oxide, 0.1% to 0.3% Lactic acid, 0.1% to 0.5% Ethylenediaminetetracetic acid, 0.1% to 0.5% Glutaraldehyde, 0.1% to 0.25% Salisept; and during which (c) the nitrile rubber latex gloves are finally placed in to packaging utilising a clear coat varnish that it is impregnated with a phenolic chlorine compound, micronised nanosilver colloid, and a quaternary compound.

In lesser forms of the invention, the type of constituents detailed under final formulation review can substitute for the specific constituents detailed there.

The invention claimed is:

1. A method of manufacturing medical examination gloves comprising:
   (a) contacting glove formers with a coagulant solution, to which has been added a composition comprising: 1% to 3% alcohol ethoxylate, 0.1% to 0.5% amine oxide, 0.1% to 0.5% ethylenediaminetetraacetic acid, 0.1% to 0.5% glutaraldehyde, 0.5% to 1% chlorhexidine di-gluconate, 0.5% to 1% chlorhexidine di-hydrochloride, 0.1% to 0.25% 4-isothiazolin-3-one-5-chloro-2-methyl-; 3(2H)-isothiazolone, less than 0.2% titanium dioxide, less than 0.2% nanoparticle silver to form coated glove formers;
   (b) contacting the coated glove formers with a nitrile rubber latex dispersion to which has been added a composition comprising: 1% to 3% alcohol ethoxylate, 0.1% to 0.5% amine oxide, 0.1% to 0.3% lactic acid, 0.1% to 0.5% ethylenediaminetetraacetic acid, 0.1% to 0.5% glutaraldehyde, 0.1% to 0.25% 4-isothiazolin-3-one-5-chloro-2-methyl-; 3(2H)-isothiazolone to form nitrile rubber latex gloves.

2. The method according to claim 1, wherein the coagulant solution in (a) further contains divalent calcium ions and calcium nitrate particles.

3. The method according to claim 1, wherein the gloves are placed in antimicrobial packaging.

4. The method according to claim 3, wherein the antimicrobial packaging contains a solution containing a phenolic chlorine compound, micronized nanosilver colloid, and a quaternary compound.

5. The method according to claim 1, wherein the medical examination gloves are selected from the group consisting of sterile and non-sterile gloves.

6. A medical examination glove, manufactured according to the method recited in claim 1.

* * * * *